United States Patent [19]
Rudolph et al.

[11] Patent Number: 5,420,244
[45] Date of Patent: May 30, 1995

[54] METHODS AND COMPOSITIONS FOR DIAGNOSING HTLV-I ASSOCIATED MYELOPATHY AND ADULT T-CELL LEUKEMIA

[75] Inventors: Donna L. Rudolph, Tucker; Renu B. Lal, Atlanta, both of Ga.

[73] Assignee: The United States of America as represented by the Department of Health and Human Services, Washington, D.C.

[21] Appl. No.: 103,742

[22] Filed: Aug. 6, 1993

[51] Int. Cl.$^6$ ............................................. A61K 37/02
[52] U.S. Cl. ................................ 530/326; 530/324; 530/325; 530/350; 530/403
[58] Field of Search ................. 530/350, 324–326, 530/403; 435/5, 974

[56] References Cited

U.S. PATENT DOCUMENTS 4,812,556  3/1989  Vahlne et al. .................. 530/324

OTHER PUBLICATIONS

Noraz et al. *Virology* 193:80–88, 1993.
Tanaka et al. *Aids Research and Human Retroviruses* 8(2):227–235, 1992.
Kira et al. *J. Neurol. Sci.* 107:98–104, 1992.
Chen et al. *Proc. natl. Acad. Sci., USA* 88:1182–1186, 1992.
Tanaka et al. *Int. J. Cancer* 48:623–630, 1991.
Okayama et al. *J. of Infect. Dis.* 163:47–52, 1991.
Smith and Green *Genes & Development* 4:1875–1885, 1990.
Tendler et al. *Proc. Natl. Acad. Sci. USA* 87:5218–5222, 1990.
Kashiwagi et al. *J. Infect. Dis.* 161:426–429, 1990.
Yokota et al. *Int. J. Cancer* 43:970–974, 1989.
Kamihira et al. *Jpn. J. Cancer Res.* 80:1066–1071, 1989.

*Primary Examiner*—Christine M. Nucker
*Assistant Examiner*—Jeffrey Stucker
*Attorney, Agent, or Firm*—Needle & Rosenberg

[57] ABSTRACT

The invention provides antigenic peptides derived from immunodominant epitopes of the HTLV-I tax or rex proteins that are immunoreactive with antibodies associated with disease in HTLV-I infected subjects. More specifically, the invention provides antigenic peptides consisting essentially of the amino acid sequences defined in the sequence listing by SEQ ID NOs: 1, 2, 3, 4, 5, 6, 7 and 8 and antigenic fragments thereof. The invention provides a method of diagnosing HTLV-I associated myelopathy (HAM) or a predisposition thereto, comprising the steps of: (a) contacting an antibody containing sample from the subject with a detectable amount of a peptide of the invention or an antigenic fragment thereof; and (b) detecting the reaction of the peptide with an antibody in the sample, the reaction indicating HTLV-I associated myelopathy or a predisposition thereto. The invention also provides a method of diagnosing adult T-cell leukemia or a predisposition thereto in a subject, comprising the steps of: (a) contacting an antibody containing sample from the subject with a detectable amount of the peptide of SEQ ID NO: 1; and (b) detecting the reaction of the peptide with an antibody in the sample, the reaction indicating adult T-cell leukemia or predisposition thereto.

8 Claims, No Drawings

METHODS AND COMPOSITIONS FOR DIAGNOSING HTLV-I ASSOCIATED MYELOPATHY AND ADULT T-CELL LEUKEMIA

BACKGROUND OF THE INVENTION

Infection by human T-cell lymphotropic virus type I (HTLV-I) is characterized by a long clinical latency; only a minor proportion (1 to 4%) of infected individuals develop disease such as adult T-cell leukemia (ATL) or HTLV-I-associated myelopathy (HAM), also known as tropical spastic paraparesis (3,30,36). ATL is an aggressive malignancy of mature T-cells frequently associated with infilterative skin lesions, lymphadenopathy, and hypercalcemia. In contrast, HAM is a chronic slowly progressive neurological condition characterized by motor weakness along with bladder and bowel dysfunction. The factors responsible for progression from latency to productive infection and manifestation of disease are still undefined. It has been suggested that activation of the lymphoid cells in the host plays a crucial role in triggering viral expression (31). Indeed, antigenic stimulation of HTLV-I infected cells in vitro results in activation of viral gene expression and replication (6,25). Collectively, differences in both functional and clinical characteristics of ATL and HAM suggest that altered viral strains, clonal expansion of infected cells or host immune responsiveness may be responsible for these clinical outcomes.

While the genetic predisposition to the disease has not been completely ruled out, genotypic analysis of the viral strains from individuals with ATL, HAM or asymptomatic carriers have demonstrated minimal sequence variations, suggesting that the viral strain itself does not appear to play a major role in the pathogenesis. Furthermore, clonal proliferation of HTLV-I-infected T-cells has not been found to be a unique feature of HAM, since asymptomatic HTLV-I-infected carriers also had frequent clonal expansion of HTLV-I-infected cells. Analysis of humoral immune responses has demonstrated elevated levels of HTLV-I-specific antibodies, however, no preferential recognition of immunodominant epitopes of the gag and env proteins in any clinical group suggested that immune responsiveness to HTLV-I structural proteins may not be associated with the disease manifestation. Alternatively, specific cellular immune responses might be responsible for the development of HTLV-I-specific disease. Indeed, elevated levels of both in vitro spontaneous proliferation (12,13) and HTLV-1-specific cytotoxic T-lymphocytes (CTL) of peripheral blood mononuclear cells (PBMC) from patients with HAM have been reported (14–16) and it has been proposed that CTL against HTLV-I proteins may contribute to the disease pathogenesis. However, recent studies demonstrating the presence of activated CTL in asymptomatic carriers 917) raises some uncertainty about their significance in the pathogenesis of the disease.

Previous studies (12,37) report a correlation between antibody to p40$^{tax}$ protein of human T cell leukemia virus 1 and infectivity, the prevalence of antibody to p42 of HTLV-I among ATL patients in comparison with healthy carriers, and hyperimmune responsiveness to HTLV-I antigens in HAM patients (19,23, respectively). It is also reported that almost all of HAM and approx 50% of ATL and asymptomatic donors have been shown to contain anti-tax antibodies (48).

Further, HTLV-I proviral DNA and RNA are detected more frequently in patients with HAM than in those of asymptomatic carriers. Recent studies have indicated that patients with HAM not only have increased HTLV-I proviral DNA load (7,14), but also enhanced viral transcription (8,33). More recently, it has been suggested that concomitant expression of mRNA specific for the regulatory proteins, pX and the upregulation of interleukin-2 (IL-2) and the α subunit of IL-2 receptor (IL-2Rα) in patients with HAM, is essential for maintaining a state of lymphocyte activation in HAM, thereby contributing to the pathogenesis of this disease (33). The data on pX expression among ATL are inconsistent; one group found increased expression (13) but others did not detect any message (22,33).

The pX gene region of HTLV-I encodes for at least two regulatory proteins, termed tax (p40$^x$) and rex (p27$^{x-III}$) (30). Both of these proteins are translated in different open reading frames from the double spliced mRNA, both are positive regulators of gene expression, and both have been implicated in viral leukemogenesis. The tax protein is a transcriptional activator that not only augments activity of its own long terminal repeat (LTR), but also induces the expression of several cellular genes, in particular those involved in T-cell activation and proliferation (30,33). In contrast, the rex protein acts at a posttranscriptional level, leading to expression of the structural gene products necessary for virion assembly (30).

The amino-terminal region of the tax protein of HTLV-I has previously been shown to contain functional domains required for the trans-activation of its own long terminal repeat (LTR) through a cyclic-AMP response element pathway, as well as selected cellular and heterologous viral promoters through activation of NF-kB (30). Mutational analysis of tax has further demonstrated that the amino acids $^{123}$ThrLeu contained within the tax8 epitope are crucial for trans-activation through both NF-kB and CRE pathways (29) and may play a role in disease pathogenesis. However, whether the carboxyl-terminus of tax protein is implicated in the transactivation function remains unclear (27,29).

Regarding the rex protein, basic amino acids at the amino terminus have been shown to be responsible both for the nuclear-nucleolar localization and for the protein's function mediated through the cis-acting RNA sequences (rex response element [RxRE]).2 Thus, while the functional domains of tax and rex have been identified (27,29,34), not much is known about the immunogenic regions of these proteins, in particular during natural infection.

Anti-tax antibodies have been shown to be associated with the increased incidence of vertical and sexual transmission of the HTLV-I (4,12). The antigenicity of the carboxyl terminal domain of tax protein has previously been suggested by virtue of rabbit antisera to the carboxyl terminus peptide or mouse monoclonal antibodies reacting with the native tax protein (29,32). A recombinant peptide of tax (Rp-F$^{329-353}$) has recently been shown to react with 42.8% of the serum specimens (20). Most of the studies analyzing anti-tax responses have utilized recombinant tax protein expressed in various expression vectors in a WB format (4,5,12,14,21,28,37,42–44). However, the results of such preparations can vary depending upon the concentration and purity of the recombinant protein used.

Thus, there exists a need for a synthetic peptide based assays to provide a method of diagnosing HAM and ATL.

SUMMARY OF THE INVENTION

The invention provides antigenic peptides derived from immunodominant epitopes of the HTLV-I tax or rex proteins that are immunoreactive with antibodies associated with disease in HTLV-I infected subjects. More specifically, the invention provides antigenic peptides consisting essentially of the amino acid sequences defined in the sequence listing by SEQ ID NOs: 1, 2, 3 and 4 and antigenic fragments thereof. These peptides correspond to the immunodominant epitopes of the tax regulatory protein of HTLV-I as further described below in the Examples.

The invention also provides antigenic peptides consisting essentially of the amino acid sequences defined in the sequence listing by SEQ ID NOs: 5, 6, 7 and 8 and antigenic fragments thereof. These peptides correspond to the immunodominant epitopes of the rex regulatory protein of HTLV-I as further described below in the Examples.

The invention also provides method of diagnosing disease caused by HTLV-I utilizing peptides of the invention. More specifically, the invention provides a method of diagnosing HTLV-I associated myelopathy (HAM) or a predisposition thereto, comprising the steps of: (a) contacting an antibody containing sample from the subject with a detectable amount of the peptide of SEQ ID NO: 2 or an antigenic fragment thereof; and (b) detecting the reaction of the peptide with an antibody in the sample, the reaction indicating HTLV-I associated myelopathy or a predisposition thereto. Alternatively, the peptides of SEQ ID NOs: 3, 4, 7 or 8, or antigenic fragments thereof can be used in the contacting step of the present method.

The invention also provides a method of diagnosing adult T-cell leukemia or a predisposition thereto in a subject, comprising the steps of: (a) contacting an antibody containing sample from the subject with a 2detectable amount of the peptide of SEQ ID NO: 1; and (b) detecting the reaction of the peptide with an antibody in the sample, the reaction indicating adult T-cell leukemia or predisposition thereto.

DETAILED DESCRIPTION OF THE INVENTION

Peptides

The invention provides antigenic peptides derived from immunodominant epitopes of the HTLV-I tax or rex proteins that are immunoreactive with antibodies associated with disease in HTLV-I infected subjects. More specifically, the invention provides antigenic peptides consisting essentially of the amino acid sequences defined in the sequence listing by SEQ ID NOs: 1, 2, 3 and 4 and antigenic fragments thereof. These peptides correspond to the immunodominant epitopes of the tax regulatory protein of HTLV-I as further described below in the Examples.

The invention also provides antigenic peptides consisting essentially of the amino acid sequences defined in the sequence listing by SEQ ID NOs: 5, 6, 7 and 8 and antigenic fragments thereof. These peptides correspond to the immunodominant epitopes of the rex regulatory protein of HTLV-I as further described below in the Examples.

The peptide or antigenic fragment of the peptide can be isolated from the protein by chemical or mechanical disruption. The peptides and fragments thus obtained can be tested to determine their antigenicity and specificity by the methods taught herein. The peptides and antigenic fragments of the invention can also be synthesized directly as described in the Examples. An antigenic fragment is defined as an amino acid sequence of at least about 5 consecutive amino acids derived from the amino acid sequence of the peptide wherein the fragments have the antigenic characteristics of the peptides. The peptides and fragments of the present invention can also be recombinant proteins obtained by cloning nucleic acids encoding the peptide in an expression system capable of producing the antigenic peptide or fragments thereof.

Once the amino acid sequence of the immunodominant regions of the protein is provided, it is also possible to synthesize, using standard peptide synthesis techniques, peptides and fragments chosen to be homologous to immunoreactive regions of the protein and to modify these peptides by addition, deletion or modification of particular amino acid residues in the derived sequences. Thus, synthesis or purification of an extremely large number of antigenic peptides consisting essentially of the disclosed amino acid sequences is possible using routine methods given the teaching herein.

The amino acid sequences of the present peptides can contain an immunoreactive portion of tax or rex attached to sequences designed to provide for some additional property, such as solubility or attachment. The amino acid sequences of the peptides can be modified to provide for some additional property, such as to remove/add amino acids capable of disulfide bonding, to increase its biolongevity, or alter enzymatic activity. In any case, the peptide must posses the bioactive property of antigenicity.

Determining antigenicity

The purified peptide fragments thus obtained can be tested to determine their antigenicity and specificity. The antigenicity of the peptides or fragments can be ascertained by determining the presence of a detectable reaction of the peptide with antibodies in samples from HTLV-I infected individuals as described in the Examples. The specificity of a putative antigenic peptide can be ascertained by testing the peptide against sera, other fluids or lymphocytes from subjects not infected with HTLV-I or from asymptomatic carriers and determining the amount of cross-reactivity of the peptide with antibodies in those samples. Methods of determining antigenicity and specificity are taught in the Examples.

Diagnostic methods

The invention also provides method of diagnosing disease caused by HTLV-I utilizing peptides of the invention.

Diagnosing HAM

More specifically the invention provides a method of diagnosing HTLV-I associated myelopathy (HAM) or a predisposition thereto, comprising the steps of: (a) contacting an antibody containing sample from the subject with a detectable amount of an antigenic peptide consisting essentially of the amino acid sequence defined in the sequence listing by SEQ ID NO: 2 or an antigenic fragment thereof; and (b) detecting the reaction of the peptide with an antibody in the sample, the reaction indicating HTLV-I associated myelopathy or a predisposition thereto. Alternatively, the peptides of SEQ ID NOs: 3, 4, 7 or 8, or antigenic fragments thereof can be used in the contacting step of the present method.

A mixture of the peptides selected from the group consisting essentially of the amino acid sequences defined in the sequence listing by SEQ ID NOs: 2, 3, 4, 7, and 8 can be used in the contacting step. This mixture can be various combinations of two, three, four or can be all five peptides. Thus, the reaction of any of the peptides in the mixture with an antibody from the subject indicates HAM or a predisposition to HAM. The method of diagnosing HAM, using a mixture of peptides can include peptides consisting essentially of the amino acid sequences defined in the sequence listing by SEQ ID NO: 2, SEQ ID NO: 3 and SEQ ID NO: 4. Detectable amounts of these peptides can be determined based on the methods taught in the Examples for determining immunoreactivity and other methods known in the art.

This method diagnoses HTLV-I associated myelopathy or a predisposition thereto in a subject by detecting an antibody from a subject that is a marker for HTLV-I associated myelopathy. A marker antibody for HAM is one that is present at higher levels in patients with HAM than in patients with ATL or in asymptomatic carriers, measured as differences in immunoreactivity of one or more of the present peptides with an antibody-containing sample from a HAM patient compared to non-HAM subjects. The differences in immunoreactivity can vary among the peptides, but must be a statistically distinguishable difference. Also, differences in immunoreactivity of HAM patient sera to the peptides can vary, as long as an average difference between levels of immunoreactivity among the different clinical groups is maintained. For example, the average difference in immunoreactivity of a panel of HAM sera against one or more of the peptides compared to reactivity of asymptomatic serum against the same peptides can range from about 33% to about 50%. In comparing HAM sera reactivity to ATL sera reactivity, the average difference in immunoreactivity against the same peptides can range from about 44% to 64%. Methods of making determinations of immunoreactivity are provided in the Examples.

Diagnosing ATL

The invention also provides a method of diagnosing adult T-cell leukemia or a predisposition thereto in a subject, comprising the steps of: (a) contacting an antibody containing sample from the subject with a detectable amount of the peptide of SEQ ID NO:1; and (b) detecting the reaction of the peptide with an antibody in the sample, the reaction indicating adult T-cell leukemia or predisposition thereto. The method works by detecting an antibody that is associated with adult T-cell leukemia. An antibody associated with ATL is one that is present at higher levels in patients with ATL than in asymptomatic carriers, measured as differences in immunoreactivity of one or more of the present peptides with an antibody-containing sample from the ATL patient compared to asymptomatic carriers. The differences in immunoreactivity can vary among the peptides and serum samples, but should provide a statistically distinguishable difference. For example, in comparing ATL sera reactivity to asymptomatic sera reactivity, the average difference in immunoreactivity ranges from about 10% to about 38%. Methods of making determinations of immunoreactivity are provided in the Examples.

Thus, the invention provides a method of distinguishing between ATL and HAM in HTLV-I infected individuals using antibody reactivity against one or more of the present peptides.

In the diagnostic methods taught herein, the peptide can be bound to a solid support (substrate) and contacted by a fluid sample such as serum, urine, or saliva. This sample can be taken directly from the patient or in a partially purified form. In this manner, antibodies to tax and rex (the primary antibody) will react with the bound peptides. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, *Antibodies: A Laboratory Manual,* Cold Spring Harbor Laboratory, Cold Spring Harbor, N.Y., 1988).

The following examples are intended to illustrate, but not limit, the invention. While they are typical of those that might be used, other procedures known to those skilled in the art may be alternatively employed.

EXAMPLE 1

Differential immune responsiveness to the immunodominant epitopes of tax and rex in HAM A. Recombinant tax fusion protein.

The plasmid expressing the recombinant fusion protein, ptaxH$_6$, was constructed as described previously (38). Plasmid ptaxH$_6$ contained the full length tax cDNA with six histidine codons appended at the end of the COOH-terminal coding sequence to facilitate tax purification by metal chelating chromatography. Expression of ptaxH$_6$ was directed by the bacteriophage T5 P21 promoter. *Escherichia coli* HB101 cells containing ptaxH$_6$ were grown, harvested, treated with EDTA/lysozyme, and sonicated. The supernatant was then precipitated with ammonium sulfate at 25% saturation. The precipitate was dissolved in buffer A (50 mM sodium phosphate, pH 7.8, 0.5M NaCl, 0.5 mM DTT, 0.5 mM PMSF, and 5 mM imidazole), loaded on a Pharmacia chelating Sepharose 6B column precharged with Ni$^{2+}$, and eluted with an imidazole gradient of 0 to 0.4M in buffer B (50 mM sodium phosphate, pH 7.2, 0.3M NaCl, and 10% glycerol). The fractions containing rtax were dialyzed against buffer C (50 mM Hepes, pH 7.9, 50 mM KCl, 0.5 mM MgCl$_2$, 0.1 mM EDTA, 0.5 mM PMSF, 0.25 mM DTT, and 20% glycerol), aliquoted, and frozen at −70° C.

B. Peptide synthesis.

Based on the sequence data for the HTLV-I tax and rex proteins (Genbank Accession #J02029), overlapping peptides were synthesized on a Applied Biosystems Models 430 or 431 peptide synthesizers with 9-fluorenylmethyloxycarbonyl chemistry, using the manufacturer's reagents and recommended chemistry cycles. Amino acid composition, sequences analysis and analytical reverse phase HPLC were performed to confirm peptide sequence and purity.

C. Antibodies to rtax in HTLV-positive specimens.

The purified rtax protein demonstrated a major band at 40 kDa, along with a minor band at 38 kDa on polyacrylamide gels. WB analysis of this protein using a rabbit antisera to the purified rtax and serum specimens from HTLV-I-infected individuals demonstrated a strong reactive band at 40 kDa. Competitive inhibition experiments using soluble rtax to compete with the serum anti-rtax antibodies completely abrogated antibody reactivity. Table 5 shows the seroreactivity of HTLV-I and HTLV-II positive specimens with the rtax.

D. Localization of immunodominant epitopes.

Serum specimens.

Serum specimens from 188 individuals previously identified to be infected with HTLV-I (n=145) or HTLV-II (n=19) or uninfected (n=24) were used to determine the immunodominant epitopes of regulatory proteins, tax and rex. Of the HTLV-I-infected specimens, 28 were from patients with HAM, 48 were from patients with ATL, and 69 were from asymptomatic blood donors. All specimens were tested by WB analysis to confirm antibodies to gag and env gene products and were typed to be infected with HTLV-I or HTLV-II by PCR or by serologic assays containing the type-specific immunodominant epitopes of HTLVs (16).

Enzyme immunoassay.

An enzyme immunoassay was developed to detect antibodies to synthetic peptides essentially as described previously (15). Briefly, polyvinyl plates were coated with 50 ul of synthetic peptides (10 μg/ml) in 0.01M carbonate buffer, pH 9.6. The plates were washed with PBS containing 0.05% Tween-20 (PBS-T) and treated with 150 ul of 5% bovine serum albumin in PBS-T for 2 h at room temperature to block excess reactive sites. After washings, 1:50 dilution of each test serum was added and plates were incubated overnight at 4° C. After six washes, alkaline phosphatase-conjugated goat anti-human IgG was added for 2 hr at room temperature, followed by the addition of p-nitrophenyl phosphate (Sigma) substrate. The plates were read with an ELISA reader (SLT Lab Instrument, Ronkonkome, Austria) at 405 nm. Seropositivity was defined as any value greater than the mean of the normal controls + two standard deviations. Antibodies to previously identified epitopes representing the immunodominant regions from the env proteins (Env1$^{191-214}$, Env5$^{242-257}$ and MTA$^{162-209}$) were determined as described previously (2,15,16).

Western blot (WB) analysis.

Purified rtax was run on 12% polyacrylamide gels (8 μg/gel) and transferred to a polyvinylydene fluoride membrane. After blocking with 5% bovine serum albumin in PBS-T for 2 hr at RT, the individual strips were then incubated with a 1:100 dilution of the test serum overnight at 4° C. After six washes in PBS-T, the strips were incubated with a 1:1000 dilution of goat anti-human IgG conjugated to alkaline phosphatase (Sigma) for 2 hr at RT, followed by color development as described previously (2).

Immunodominant epitopes of tax protein.

Using the purified rtax protein in an enzyme immunoassay format described above, antibodies to rtax were detected in 37 of 94 (39%) HTLV-I-positive serum specimens. Of these 37 rtax-reactive specimens, 30 specimens with larger volumes were used to examine the antibody reactivity to a set of overlapping synthetic peptides representing the entire tax protein. Such analysis identified at least two epitopes present in these peptides that reacted with >60% of rtax-positive serum samples. First, tax8, encompassing amino acid residues 106–125, reacted with 19 of 30 (63%) rtax-positive specimens. A second major immunodominant epitope(s) located near the carboxyl terminus of protein, and contained within tax22 (a.a. 316–335), tax23 (a.a. 331–350), and tax24 (a.a. 336–353), reacted with 22 of 30 (73%), 29 of 30 (97%), and 29 of 30 (97%) specimens, respectively. By correlating the relative reactivities of the overlapping peptides, three linear epitopes can be tentatively localized to amino acids 111–120 (KYSPSR-NGYM-SEQ ID NO: 38), amino acids 331–341 (HEP-QISPGGLE-SEQ ID NO: 39) and amino acid 336–350 (SPGGLEPPSEKHFRE-SEQ ID NO: 40) (Table 1). Peptides consisting essentially of these sequences can be effective in the EIA, WB and other methods of the invention. Secondary structure analysis of the tax protein demonstrated that the carboxyl terminus is hydrophilic in nature and is predicted to fold as an α-helix.

Immunodominant epitopes of rex protein.

serum specimens from HTLV-I-positive individuals (n=99) were used to determine antibody reactivity with an overlapping set of synthetic peptides representing the entire rex protein. The predominant epitope (rex1$^{1-20}$), reacting with 63% of the specimens, was located near the extreme amino terminus of the rex protein (Table 2). Three additional peptides at the amino terminus (rex2$^{16-35}$, rex4$^{46-65}$ and rex6$^{76-95}$) all reacted with 26% to 29% of HTLV-I-positive specimens; none of the other peptides gave significant reactivities. Secondary structure analysis indicated that while the extreme amino terminus is hydrophilic, other regions including rex2, 4, and 6 are not.

Interestingly, no antibodies were found to rex5, which contains the amino acid $^{70}$Ser that has recently been shown to be the phosphorylation site that regulates the rex function in response to extracellular stimuli (1).

Competitive inhibition by synthetic peptides.

Peptide competition experiments were performed using both ELISA and WB assays. For ELISA, test sera combined with various amounts of competing peptides (0, 10, 100, 250 μg/well) were incubated for 2 hr at RT, prior to addition to the rtax coated plate wells (1 μg/ml). After 2 hr incubation at RT, plates were washed in PBS-T, and assay proceeded as described above. For WB assay, the sera were incubated with purified rtax protein (10 ug/well) or synthetic tax peptide (100 ug/well) for 30 min at room temperature. The sera were then added to the WB strips containing the rtax antigen, and the assay was performed as described above.

Competitive inhibition experiments demonstrated that a combination of peptides tax22, tax23, tax24 inhibited binding of antibodies to rtax in a WB assay, whereas tax8 did not abrogate the binding of antibodies in patient's sera, suggesting that the epitope(s) from the carboxyl terminus is the major immunodominant epitope of the HTLV-I tax protein. To further define the amino acids within the carboxyl terminus of tax that are recognized by sera from HTLV-I-infected individuals, increasing amounts of tax22, tax23 and tax24 peptides were used as competitors for binding of HTLV-I-infected sera (n=5) to rtax in an ELISA format. Maximum inhibition was obtained by tax22 (28% to 47%) in a dose dependent manner, whereas tax23, and tax24 inhibited the binding by 10% to 21%, suggesting that there are at least two linear epitopes, one of which (tax22) has a high affinity for anti-tax antibodies. Incubation of env peptide (Env1) with the HTLV-I-infected sera did not affect the binding to rtax, further confirming the specificity of peptide inhibition.

E. Correlation of immune responses to immunodominant epitopes in clinical groups.

To determine if different immune reactivities to the immunodominant epitopes of regulatory proteins existed in clinical groups, we tested serum specimens from patients with HAM (n=28) or ATL (n=48) and from asymptomatic HTLV-I-I-carriers (n=69) by WB analysis with purified recombinant tax protein and by using synthetic peptides representing the immunodominant epitopes. The percent seroreactivity to rtax in WB assay was 96% (27 of 28) for patients with HAM, 42% (20 of 48) for ATL, and 59% (41 of 69) for asymptomatic carriers; minimal cross-reactivity was observed for asymptomatic carriers infected with HTLV-II (5%). Similar to WB results with rtax, the percent seroreactivity to synthetic tax8, tax22, tax23, and tax24 was highest (71% to 93%) in patients with HAM, followed by reactivity in asymptomatic carriers (25% to 39%) and patients with ATL (4% to 31%) (Table 3). Interestingly, while the carboxyl terminal peptides of tax had minimal reactivity (4% to 17%) with sera from ATL patients, tax8 reacted with 31% of these sera. The seroreactivity to a combination of the carboxyl terminus peptides (tax 22, tax23, tax24) in sera from HAM patients (96%) or from the asymptomatic HTLV-I-infected persons (52%) was comparable to that obtained by recombinant WB assays (96% and 59%, respectively). However, tax reactivity in sera from ATL patients was apparently directed predominantly against the tax8 epitope (31%), since the combined tax22, tax23, tax24 reactivity was lower (17%) when compared with results of the rtax assay (42%).

Similarly, differential immune reactivities were observed for rex epitopes; rex4, and rex6 demonstrated predominant reactivities in HAM patients (52%) when compared with ATL patients (19% to 24%) and asymptomatic carriers (7 to 23%). In contrast, rex2 had increased percent reactivity in asymptomatic carriers (43%) compared with that of HAM (15%) or ATL (29%) patients; no difference in antibody reactivity to rex1 was observed in either group (data not shown).

Since patients with HAM have higher levels of antibodies in general, we questioned whether preferential recognition of tax and rex epitopes was a mere reflection of higher levels of antibodies in this group of patients. Parallel analysis of antibodies to previously identified env epitopes (recombinant MTA[162-209] synthetic Env1[191-214], synthetic Env5[242-257]) showed similar reactivities in all three groups. In contrast, preferential responses were observed to all tax epitopes (tax8, tax22, tax23, tax24) and two rex epitopes (rex4 and rex6) in the HAM group, followed by the asymptomatic and ATL groups; seroreactivity of rex1 was similar in both the HAM and asymptomatic groups. These results indicate that preferential recognition of tax and rex proteins in patients with HAM reflects differential immune responsiveness to these viral regulatory proteins, as compared with structural proteins.

Sequence analysis demonstrated that HTLV-II tax lacks the corresponding 22 amino acids from the C-terminus (9). The existence of an immunodominant C-terminus domain that is dispensable for the functional aspect of tax protein raises the possibility that this domain may be associated with or responsible for the development of disease during HTLV-I infection. The present results show that hyperimmune responsiveness to HTLV-I antigens in HAM patients extends to the regulatory proteins, including tax (14).

Analysis of antibody responses to the individual immunodominant epitopes from the regulatory proteins delineated the antigenic availability of these proteins in vivo and their potential role in disease progression. More importantly, the levels of antibody reactivities differed strikingly from the reactivities to the HTLV-I structural proteins. While almost all HTLV-I-infected individuals produced antibodies to the structural proteins, represented by env epitopes (MTA, Env1, Env5), only some individuals responded to tax and rex. The lack of differential immune responsiveness to structural proteins among any of the clinical groups suggests that differential immune responses to the regulatory proteins may be associated with disease expression. It is possible that increased transcription of tax and rex message could lead to increased production of antigen and eventual antibody production in this group of patients. The lack of immune responsiveness to tax and rex epitopes in patients with ATL in our study suggests lower expression of tax and rex in vivo.

The fact that regulatory proteins of HTLV-I elicit an antibody response raises the interesting question of how these intracellular proteins become available to the immune system. Virus-induced cytopathicity and cell lysis by cytotoxic T-cells are likely to facilitate such antigens being presented to the immune system. Indeed, tax-specific cytotoxic T-cell responses have been demonstrated in both HAM and ASY patients (10,11,24). Alternatively, tax and rex could become extracellular by secretion from infected cells. Neither tax nor rex contain a conventional secretory signal sequence; in fact, both of these proteins contain sequences that direct them toward the nucleus (27,29). However, recent studies demonstrating the presence of soluble tax in culture supernatants from HTLV-I-infected cell lines which stimulates proliferation of primary lymphocytes in cultures suggest the extracellular presence of tax (18). The presence of rex in the supernatants from HTLV-I-infected cell lines has yet to be demonstrated.

In summary, tax and rex antibodies are produced in a subset of individuals infected with HTLV-I. This finding is not representative of the humoral antiviral response, as all infected individuals contain antibody responses to structural viral proteins. Intermittent cytotoxic T-lymphocyte activity in HAM patients could explain the availability of viral regulatory proteins for stimulation of antibody production.

TABLE 1

Seroreactivity of HTLV-I specimens with overlapping synthetic peptides from the p40$^{tax}$ protein of HTLV-I.

| Peptide name | A.A. no | Sequence | seroreactivity (%) | SEQ.ID NO.'s |
|---|---|---|---|---|
| Tax1 | 1-20 | MAHFPGFGQSLLFGYPVYVF8 | 0/30 (0) | 9 |
| Tax2 | 16-35 | PVYVFGDCVQGDWCPISGGL | 0/30 (0) | 10 |
| Tax3 | 31-50 | ISGGLCSARLHRHALLATCP | 2/30 (7) | 11 |
| Tax4 | 46-65 | LATCPEHQITWDPIDGRVIG | 1/30 (3) | 12 |
| Tax5 | 61-80 | GRVIGSALQFLIPRLPSFPT | 0/30 (0) | 13 |
| Tax6 | 76-95 | PSFPTQRTSKTLKVLTPPIT | 0/30 (0) | 14 |
| Tax7 | 91-110 | TPPITHTTPNIPPSFLQAMR | 0/30 (0) | 15 |
| Tax8 | 106-125 | LQAMRKYSPFRNGYMEPTLG | 19/30 (63) | 1 |
| Tax9 | 121-140 | EPTLGQHLPTLSFPDPGLRP | 0/30 (0) | 16 |
| Tax10 | 136-155 | PGLRPQNLYTLWGGSVVCMY | 3/19 (16) | 17 |
| Tax11 | 151-170 | VVCMYLYQLSPPITWPLLPH | 7/30 (23) | 18 |
| Tax12 | 166-185 | PLLPHVIFCHPGQLGAFLTN | 1/19 (5) | 19 |
| Tax13 | 181-200 | AFLTNVPYKRIEELLYKISL | 0/30 (0) | 20 |
| Tax14 | 196-215 | YKISLTTGALIILPEDCLPT | 1/19 (5) | 21 |
| Tax15 | 211-230 | DCLPTTLFQARAAPVTLTAW | 1/19 (5) | 22 |
| Tax16 | 226-245 | TLTAWQNGLLPFHSTLTTPG | 1/19 (5) | 23 |
| Tax17 | 241-260 | LTTPGLIWTFTDGTPMISGP | 0/30 (0) | 24 |
| Tax18 | 256-275 | MISGPCPKDGQPSLVLQSSS | 1/30 (3) | 25 |
| Tax19 | 271-290 | LQSSSFIFHKFQTKAYHPSF | 0/30 (0) | 26 |
| Tax20 | 286-305 | YHPSFLLSHGLIQYSSFHSL | 0/30 (0) | 27 |
| Tax21 | 301-320 | SFHSLHLLFEEYTNIPISLL | 0/30 (0) | 28 |
| Tax22 | 316-335 | PISLLFNEKEADDNDHEPQI | 22/30 (73) | 2 |
| Tax23 | 331-350 | HEPQISPGGLEPPSEKHFRE | 29/30 (97) | 3 |
| Tax24 | 336-353 | SPGGLEPPSEKHFRETEV | 29/30 (97) | 4 |

TABLE 2

Seroreactivity of HTLV-I specimens with overlapping synthetic peptides covering the p27$^{rex}$ protein of HTLV-I.

| Peptide | A.A. no | Sequence | Seroreactivity no tested = 99 # positive (%) | SEQ ID. NOs. |
|---|---|---|---|---|
| rex1 | 1-20 | MPKTRRRPRRSQRKRPPTPW | 63 (63) | 5 |
| rex2 | 16-35 | PPTPWPTSQGLDRVFFSDTQ | 29 (29) | 6 |
| rex3 | 31-50 | FSDTQSTCLETVYKATGAPS | 15 (15) | 29 |
| rex4 | 46-65 | TGAPSLGDYVRPAYIVTPYW | 29 (29) | 7 |
| rex5 | 61-80 | VTPYWPPVQSIRSPGTPSMD | 14 (14) | 30 |
| rex6 | 76-95 | TPSMDALSAQLYSSLSLDSP | 26 (26) | 8 |
| rex7 | 91-110 | SLDSPPSPPREPLRPSRSLP | 7 (7) | 31 |
| rex8 | 106-12 | SRSLPRQSLIQPPTFHPPSS | 11 (11) | 32 |
| rex9 | 121-140 | HPPSSRPCANTPPSEMDTWN | 4 (4) | 33 |
| rex10 | 136-155 | MDTWNPPLGSTSQPCLFQTP | 11 (11) | 34 |
| rex11 | 151-170 | LFQTPDSGPKTCTPSGEAPL | 12 (12) | 35 |
| rex12 | 166-185 | GEAPLSACTSTSFPPPSPGP | 2 (2) | 36 |
| rex13 | 177-189 | SFPPPSPGPSCPT | 1 (1) | 37 |

TABLE 3

Seroreactivity of HTLV-I- and HTLV-II- positive specimens with p40$^{tax}$ peptides representing the immunodominant epitopes

| Group | Seroreactivity to synthetic peptides (%) | | | | | rtax WB reactivity |
|---|---|---|---|---|---|---|
| | Tax8 | Tax22 | Tax23 | Tax24 | Tax22-24 | |
| HAM (n = 28) | 21 (75) | 20 (71) | 26 (93) | 24 (86) | 27 (96) | 27 (96) |
| ATL (n = 48) | 15 (31) | 2 (4) | 5 (10) | 7 (15) | 8 (17) | 20 (42) |
| Asymptomatic HTLV-I (n = 69) | 24 (35) | 17 (25) | 27 (39) | 24 (35) | 36 (52) | 41 (59) |
| HTLV-II (n = 19) | 1 (5) | 0 (0) | 0 (0) | 0 (0) | 1 (5) | 1 (5) |
| Controls (n = 24) | 0 (0) | 0 (0) | 0 (0) | 0 (0) | 0 (0) | 0 (0) |

TABLE 4

| Synthetic peptides | Seroreactivity # positive (%) | | |
|---|---|---|---|
| | HAM (n = 27) | ATL (n = 42) | ASY (n = 30) |
| Tax epitopes: | | | |
| Tax8$^{106-125}$ | 21 (78) | 15 (36) | 10 (33) |
| Tax22$^{316-335}$ | 19 (70) | 2 (5) | 8 (27) |
| Tax23$^{331-350}$ | 25 (93) | 5 (12) | 11 (37) |
| Tax24$^{336-313}$ | 23 (85) | 7 (17) | 11 (37) |
| Rex epitopes: | | | |
| Rex1$^{1-20}$ | 22 (81) | 17 (40) | 21 (70) |
| Rex2$^{16-35}$ | 4 (15) | 12 (29) | 13 (43) |
| Rex4$^{46-65}$ | 14 (52) | 8 (19) | 7 (23) |
| Rex6$^{76-95}$ | 14 (52) | 10 (24) | 2 (7) |

TABLE 5

Seroreactivity of HTLV-I and HTLV-II positive specimens with the recombinant tax protein

| Specimens | No. tested | rTax reactivity # pos | rTax reactivity % reactivity |
|---|---|---|---|
| HTLV-I HAM/TSP | 28 | 27 | 96 |
| ATL | 48 | 20 | 42 |
| Asymptomatic Blood Donors | 69 | 41 | 59 |
| HTLV-II | 19 | 1 | 5 |

EXAMPLE 2

Detection of Antibodies to p40$^{taxI}$ Of HTLV-I by a synthetic peptide-based assay Antibodies to human T-cell lymphotropic virus type I (HTLV-I) trans-activator protein p40$^{taxI}$) were determined in serum specimens from individuals infected with HTLV-I (n=138) and HTLV-II (n=19). Western blot analysis using recombinant tax (rtax) demonstrated the presence of anti-tax antibodies in 96% (25/26) of patients with HTLV-I-associated myelopathy (HAM), 43% (20/46) of those with adult T-cell leukemia (ATL) and 61% (40/66) of asymptomatic HTLV-I blood donors; only one of the HTLV-II specimens reacted with the rtax protein. Synthetic peptides (tax8$^{106-125}$, tax22$^{316-335}$, tax23$^{331-350}$, and tax-24$^{336-353}$) representing the immunodominant epitopes of p40$^{taxI}$, detected anti-tax antibodies in 66 (48%), 50 (36%), 66 (48%) and 64 (46%) of 138 HTLV-I positive specimens, respectively. An enzyme immunoassay using an equimolar ratio of these four peptides allowed sensitive detection of anti-tax antibodies in 96% (25/26) of patients with HAM, 52% (24/46) of ATL, and 62% (41/66) of asymptomatic HTLV-I-infected donors. The synthetic peptide-based cocktail assay was HTLV-I specific, since none of the HTLV-II infected specimens reacted with these peptides. Interestingly, the corresponding regions from the HTLV-II tax protein, tax8II$^{106-125}$ and tax-22II$^{312-331}$ did not react with either HTLV-II or HTLV-I specimens. Thus, a synthetic peptide-based assay comprising immunodominant epitopes located towards the amino-terminus and at the C-terminus of p40$^{taxI}$ provides a reliable and sensitive assay for the detection of anti-tax antibodies in seroepidemiologic studies.

A. Immune reactivity to rtax.

The plasmid expressing the tax fusion protein, ptax-H$_6$was constructed as described previously (38). Immune reactivity to the recombinant tax (rtax) protein was determined both by enzyme immunoassay (EIA) and by Western blotting (WB) assay.

Enzyme immunoassay.

For the EIA, 50 ul of purified rtax protein was coated on to polyvinyl plates at a concentration of 1 ug/ml in 0.1M carbonate buffer, pH 9.6. The excess reactive sites were blocked by the addition of 5% bovine serum albumin (BSA) in phosphate-buffered saline (pH 7.4), containing 0.1% Tween-20 (PBS-T), followed by the addition of a 1:50 dilution of test sera and plates were incubated overnight at 4° C. After six washes, a 1:1000 dilution of alkaline phosphatase-conjugated goat anti-human IgG (Sigma, St Louis, Mo.) was added for 2 hours at RT, followed by six washes and then the addition of p-nitrophenyl phosphate (Sigma) substrate. The plates were read after one hour with an ELISA reader (SLT Lab Instrument, Ronkonkome, Austria) at 405 nm. Seropositivity was defined as any value greater than the mean of the normal controls +2 standard deviations.

Western blot.

For WB analysis, rtax protein was run on 12% polyacrylamide gels (8 μg/gel) and transferred to a polyvinylydene fluoride (PVDF) membrane. After blocking with 5% BSA in PBS-T for 2 hours at RT, the individual strips were incubated with a 1:100 dilution of either rabbit anti-tax antisera (obtained through the AIDS Repository) or the test serum overnight at 4° C. After 3 washes, the strips were incubated with a 1:1000 dilution of goat anti-human IgG or goat anti-rabbit IgG conjugated to alkaline phosphatase for 2 hours at RT, followed by color development with the BCIP/NBT phosphatase substrate system (Kirkegaard & Perry, Gaithersburg, Md.).

Competitive inhibition.

Inhibition of antibody binding to the rtax protein was carried out by adding rtax protein or synthetic tax peptide to the sera before their addition to the assay. In the EIA, diluted sera was incubated with the peptides at a concentration of 100, 10, and 1 μg/well for 2 hours at RT before addition to the ELISA plate. The assay was then carried out as previously described. In the WB assay, the serum was mixed with the inhibition antigen (rtax 10 μg/well) for 30 minutes at RT before it was added to the WB strip containing the rtax antigen, and followed by assay as described above.

Antibodies to rtax in HTLV-positive specimens.

An EIA with the purified rtax protein demonstrated antibodies to tax in serum specimens from 23 of 26 (88%) individuals with HAM, 11 of 46 (24%) of those with ATL, and 37 of 66 (56%) of asymptomatic HTLV-I infected blood donors (Table-1), suggesting that antibodies to rtax could be detected in individuals infected with HTLV-I. The purity of the rtax was confirmed by the detection of a major band at 40 kD by rabbit polyclonal antisera raised against the tax protein in the WB. The specificity of the anti-tax antibodies was confirmed by competitive inhibition experiments, where addition of soluble rtax protein was able to completely block the binding of antibodies to the rtax protein on the WB strip in a dose dependent manner. WB analysis using rtax resulted in an enhanced sensitivity of anti-tax antibody detection; 96% of the specimens from HAM patients (25/26), 43% of the specimens from ATL patients (20/46) and 61% of those from asymptomatic carriers (40/66) demonstrated anti-tax antibodies (Table-1). Further, detection of anti-tax antibodies appeared to be HTLV-I type specific, since only one of the specimens from individuals infected with HTLV-II demonstrated any reactivity to the rtax in either EIA or WB (Table-1).

The relative antibody reactivities to highly purified rtax seemed to be higher with denatured forms of the antigen in the WB format (62%) than with non-denatured forms in the EIA (51%). The chemical denaturation of the protein might expose certain epitopes not available when EIA plates are coated. Alternatively, the reactivities to rtax in serum specimens from HTLV-I-infected individuals may be conformation-dependent.

B. Synthetic peptide based Immunoassay.

Peptide synthesis.

The peptides were synthesized by FMOC chemistry, analyzed and purified as previously described (46). As described above, the peptides derived from the HTLV-I sequence were tax-8$^{106-125}$, tax-22$^{316-335}$, tax-23$^{331-350}$ and tax24$^{336-353}$. To determine the type-specificity of these immunogenic regions, corresponding regions from HTLV-II, tax8II[106-125] and tax-22II[312-331], were also synthesized.

An EIA was developed using these synthetic peptides essentially as described for rtax, except that the polyvinyl plates were coated with 50 ul of tax8, tax22, tax23, tax24, tax8II or tax22II peptides (10 µg/ml) either separately or in combination.

Serum specimens.

Serum specimens from 176 individuals previously identified to be infected with HTLV-I (n=138), or HTLV-II (n=16) were used to analyze antibodies to tax. Serum specimens from 22 blood donors previously shown to be negative for antibodies to HTLV-I and HTLV-II were included as controls. Of the HTLV-I-infected specimens, 26 were from patients with HAM, 46 were from patients with ATL and 66 were from asymptomatic blood donors. All of the HTLV-II specimens were IVDUs from the United States. All of the specimens were tested by WB to confirm the presence of antibodies to both gag and env gene products, and were typed to be infected with HTLV-I or HTLV-II by the polymerase chain reaction (PCR) or by serologic assays containing type-specific immunodominant epitopes of HTLV-I and -II, as described previously (16,47).

Immunogenicity and type-specificity of tax epitopes.

We have recently identified major immunodominant epitope(s), located towards the amino-terminus (a.a. 106–125) and at the C-terminus (a.a. 316–353) of the tax protein (Example 1). Synthetic peptides representing these epitopes from the tax protein of HTLV-I were used to determine the immunoreactivity of these regions and corresponding regions from the HTLV-II tax protein were analyzed to determine the viral type specificity of these epitopes. Analysis of synthetic peptides from the HTLV-I tax protein (tax8[106-125], tax22[316-335], tax23[331-350], and tax24[336-353]) with 138 HTLV-I-infected specimens demonstrated antibodies in 66 (48%), 50 (36%), 66 (48%) and 64 (46%) specimens, respectively. Immune reactivities to the four peptides were highest in patients with HAM, followed by asymptomatic individuals and patients with ATL. Furthermore, patients with ATL as a group revealed higher immune reactivity to tax8, when compared to tax22, tax23, or tax24.

Synthetic peptides from the corresponding regions of the HTLV-II tax protein were analyzed to determine the type specificity of these epitopes. None of the serum specimens from HTLV-II infected individuals demonstrated antibodies to either tax8II[106-125] or tax22II[312-331], suggesting that these epitopes presumably do not represent linear epitopes of the HTLV-II tax protein. To further examine the type specificity of the tax epitopes, competitive inhibition experiments were performed with serum specimens from six HTLV-I-infected individuals by preincubating the serum specimen with tax8, tax22, tax8II, and tax22II. The antibody reactivity against the rtax protein could be specifically inhibited by preincubation of sera with tax22 in a dose dependent manner, whereas incubation with tax8 resulted in marginal inhibition and incubation with tax8II and tax22II resulted in no inhibition at all.

Synthetic peptide EIA.

The preferential immunoreactivity to synthetic peptides representing the amino-terminus and the C-terminus of the tax protein, together with our recent report demonstrating that a cocktail representing a mixture of two peptides from the immunodominant regions of the env protein is more sensitive for detection of anti-env antibodies than either peptide alone (46), led us to examine a combination of tax22, tax23, and tax24 for anti-tax antibody detection. In general, a combination of the three peptides in equimolar ratios resulted in increased sensitivity of anti-tax antibody detection when compared to any of the peptides alone. While the combined seroreactivity to tax22, tax23, and tax24 was comparable to rtax antibody in patients with HAM (92% in peptide assay vs 96% in rtax WB assay) and asymptomatic carriers (56% in peptide assay vs 61% in rtax WB assay), peptide reactivity was significantly lower in patients with ATL (28%), when compared to the rtax WB assay (43%) (Table-1). Neither conjugation of the peptides to bovine serum albumin nor changing the molar ratio of the mixture of peptides resulted in enhanced sensitivity of detection of anti-tax antibodies (data not shown).

Since we had observed higher reactivities to tax8 in ATL patients, we next examined seroreactivity of HTLV-I specimens to tax8 in conjunction with tax22, tax23, and tax24. An equimolar ratio of these four peptides resulted not only in increased optical densities but also enhanced sensitivity of detection in all three clinical groups. More importantly, the combined seroreactivity to these peptides in HAM (96%), ATL (52%) and asymptomatic carriers (62%) was even higher than that observed for the rtax WB assay (96%, 43%, and 61%, respectively) (Table-1). In addition, all of the specimens that reacted on the rtax WB assay also reacted with this peptide assay. Further, the antibody responses to this peptide mixture were also type specific, since none of the HTLV-II serum specimens reacted in this assay.

Only one of the serum specimens from individuals infected with HTLV-II reacted with the rtax protein of HTLV-I. This suggests that the two tax antigens share little antigenic homology, although the p40$^{taxI}$ and p38$^{taxII}$ proteins share significant homologies (about 75%) at the nucleotide sequence level (9). However, the sequence analysis demonstrated that the HTLV-II tax contains a stop codon which results in a protein that is 22 amino acids shorter than its counterpart HTLV-I tax protein (9,30). The fact that the C-terminus of p40$^{taxI}$ contains the immunodominant epitope(s) and that the p38$^{taxI}$ lacks this motif may account for the type-specific responses to the rtax protein. In addition, the C-terminus of the HTLV-II tax protein does not appear to contain a linear epitope that elicits an antibody response, since synthetic peptide (tax22-II[312-331] representing the C-terminus of truncated p38$^{taxII}$ was not immunoreactive with serum specimens from individuals infected with HTLV-II.

The present invention provides a synthetic peptide-based assay that provides a simple tool to analyze anti-tax antibodies in individuals infected with HTLV-I. The assay is capable of detecting antibodies in all the individuals where anti-tax was detected by the WB assay and is type specific for HTLV-I infection. Thus, the assay provides a simple format to analyze anti-tax antibodies for sero-epidemiologic studies to determine markers of infectivity, but also for intrafamilial studies to determine tax antibodies among blood relatives of ATL patients.

TABLE 6

Seroreactivity of HTLV-I and HTLV-II positive specimens with the rtax protein and synthetic peptides

| Specimens | # tested | rTax reactivity EIA | rTax reactivity WB # pos (%) | Synthetic peptide reactivity (Tax22,23,24) | Synthetic peptide reactivity (Tax8,22,23,24) # pos (%) |
|---|---|---|---|---|---|
| HTLV-I: | | | | | |
| HAM | 26 | 23 (88) | 25 (96) | 24 (92) | 25 (96) |
| ATL | 46 | 11 (24) | 20 (43) | 13 (28) | 24 (52) |
| Asymptomatic | 66 | 37 (56) | 40 (61) | 37 (56) | 41 (62) |
| HTLV-II: | | | | | |
| Asymptomatic | 16 | 0 (0) | 1 (6) | 1 (6) | 0 (0) |
| Uninfected: | 21 | 0 (0) | 0 (0) | 0 (0) | 0 (0) |

Throughout this application various publications are referenced by numbers within parentheses. The disclosures of these publications in their entireties are hereby incorporated by reference into this application in order to more fully describe the state of the art to which this invention pertains. Full citations for these publications are as follows:

References

1. Adachi, Y., T. D. Copeland, C. Takahashi, T. Nosaka, A. Ahmed, S. Oroszlan, and M. Hatanaka M. 1992. Phosphorylation of the rex protein of human T-cell leukemia virus type I. J. Biol. Chem. 267:21977–21981.
2. Buckner, C., C. R. Roberts, S. K. H. Foung, J. Lipka, G. R. Reyes, K. Hadlock, L. Chan, R. A. Gongora-Biachi, B. Hjelle, and R. B. Lal. 1992. Immune responsiveness to the immunodominant recombinant envelope epitopes of HTLV-I and HTLV-II in diverse geographic populations. J. Infect. Dis. 166:1160–1163.
3. Centers for Disease Control. 1990. Human T-lymphotropic virus type-1 screening in volunteer blood donors-United States-1989. Morb. Mort. Weekly Rep, 39:915, 921–4.
4. Chen, Y. M. A., A. Okayama, T. H. Lee, N. Tachibana, N. Mueller, and M. Essex. 1991. Sexual transmission of human T-cell leukemia virus type I associated with the presence of anti-tax antibody. Proc. Natl. Acad. Sci., USA. 88:1182–1186.
5. Ehrlich, G. D., J. B. Glaser, M. A. Abbott, D. J. Slamon, D. Keith, M. Sliwkowski, J. Brandis, E. Keitelman, Y. Teramoto, L. Papsidero, H. Simpkins, J. J. Sninsky, and B. Poiesz. 1989. Detection of anti-HTLV-I tax antibodies in HTLV-I enzyme-linked immunosorbent assay-negative individuals. Blood 74:1066–1072.
6. Gazzolo, L., and M.D. Dodon. 1991. Molecular and cellular events at the onset of the lymphoproliferative process induced by HTLV-I (Human T-cell leukemia virus, type I). Bull Cancer 78:291–298.
7. Gessain, A., F. Saal, 0. Gout, M. T. O'Daniel, G. Flandrin, G. deThe, J. Peries, and F. Sigaux. 1990. High human T-cell lymphotropic virus type-I proviral DNA load with polyclonal integration in peripheral blood mononuclear cells of French West Indian, Guineas and African patients with tropical spastic paraparesis. Blood 75:428–433.
8. Gessain, A,. A. Louie, 0. Gout, R. C. Gallo, and G. Franchini. 1991. Human T-cell leukemia-lymphoma virus type I (HTLV-I) expression on fresh peripheral blood mononuclear cells from patients with tropical spastic paraparesis/ HTLV-I-associated myelopathy. J. Virol 65:1628–1633.
9. Haseltine, W. A., J. G. Sodroski, R. Patarca, D. Briggs, D. Perkins, and F. Wong-Staal. 1984. Structure of the 3' terminal region of type II human T lymphotropic virus: Evidence for a new coding region. Science 225:419–421.
10. Jacobson, S., J. Reubin, R. Streilein, and T. Palker. 1991. Induction of CD4+HTLV-I specific cytotoxic T lymphocytes from patient with HAM/TSP: recognition of an immunogenic region of the gp46 envelope glycoprotein of HTLV-I. J. Immunol. 146:1155–1162.
11. Kannagi, M., H. Shida, H. Igarashi, K. Kuruma, H. Mural, Y. Aono, I. Maruyama, M. Osame, T. Hattori, H. Inoko, and S. Harada. 1992. Target epitopes in the tax protein of human T-cell leukemia virus type I recognized by class I major histocompatibility complex-restricted cytotoxic T cells. J. Virol. 66:2928–2933.
12. Kashiwagi, S., W. Kajiyama, J. Hayashi, A. Noguchi, K. Nakashima, H. Nomura, H. Ikematsu, T. Sawada, S. Kida, and A. Koide. 1990. J. Infect. Dis. 161:426–429.
13. Kinoshita, T., M. Shimoyama, K. Tobinai, M. Ito, S. Ikeda, K. Tajima, K. Shimotohno and T. Sugimura. 1989. Detection of mRNA for the $tax_1/rex_1$ gene of human T-cell leukemia virus type I in fresh peripheral blood mononuclear cells of adult T-cell leukemia patients and viral carriers by using the polymerase chain reaction. Proc. Natl. Acad. Sci., USA 86:5620–5624.
14. Kira, J., M. Nakamura, T. Sawada, Y. Koyanagi, N. Ohori, Y. Itoyama, N. Yamamoto, Y. Sakaki, and I. Goto. 1992. Antibody titers to HTLV-I-p40$^{tax}$ protein and gag-env hybrid protein in HTLV-I-associated myelopathy/tropical spastic paraparesis: correlation with increased HTLV-I proviral DNA load. J. Neuro. Sci. 107:98–104.
15. Lal, R. B., D. L. Rudolph, M.D. Lairmore, R. F. Khabbaz, M. Garfield, J. E. Coligan, and T. M. Folks. 1991. Serologic discrimination of HTLV-I and HTLV-II infection by using a synthetic peptide-based enzyme immunoassay. J.Infect. Dis. 163:41–46.
16. Lal, R. B., D. L. Rudolph, J. E. Coligan, S. K. Brodine, and C. R. Roberts. 1992. Failure to detect evidence of human T-lymphotropic virus (HTLV) type I and type II in blood donors with isolated gag antibodies to HTLV-I/II. Blood 80:544–550.
17. Lal, R. B., C. Buckner, R. F. Khabbaz, J. Kaplan, G. Reyes, K. Hadlock, J. Lipka, S. K. H. Foung, L. Chan, J. E. Coligan. 1993. Isotypic and IgG subclass restriction of the humoral immune responses to human T-lymphotropic virus type-I. Clin. Immunol. Immunopathol. 67:40–49.
18. Marriot, S. J., P. F. Lindholm, R. L. Reid, and J. N. Brady. 1991. Soluble HTLV-I tax1 protein stimulates proliferation of human peripheral blood lymphocytes. New Biologist. 3:678–686.
19. Nakamura, M., Y. Itoyama, M. Kuroki, S. Nakano, S. Kondoh, S. Nagafuchi, J. Kira, I. Ichinose, K. Mitsugi, K. Anzai, H. Mori, M. Fukui, S. Okamura, and Y. Niho. 1992. Increase of peripheral B lymphocytes committed to the production of monoreactive and high affinity antibodies to HTLV-I in patients with HAM/TSP. J. Neuroimmunol. 37:35–45.
20. Noraz, N., S. Benichou, P. Madaule, P. Tiollais, J. C. Vernant, and C. Desgranges. 1993. Expression of HTLV-I Env and tax recombinant peptides in yeast: identification of immunogenic domains. Virol. 193:80–88.
21. Okayama, A., Y. A. Chen, N. Tachibana, S. Shioiri, T. H. Lee, K. Tsuda, and M. Essex. 1990. High incidence of antibodies to HTLV-I tar in blood relatives of adult T cell leukemia patients. J. Infect. Dis. 163:47–52.
22. Orita, S., S. Takagi, A. Saiga, N. Minoura, K. Araki, K. Kinoshita, T. Kondo, Y. Hinuma, and H. Igarashi. 1992. Human T cell leukaemia virus type 1 p21X mRNA: constitutive expression in peripheral blood mononuclear cells of patients with adult T cell leukemia. J. Gen. Virol. 73:2283–2289.
23. Osame, M., M. Matsumoto, K. Usuku, S. Izumo, N. Ijichi, H. Amitani, M. Tara, and A. Igata. 1987. Chronic progressive myelopathy associated with elevated antibodies to human T-lymphotropic virus type I and adult T-cell leukemia like cells. Ann. Neurol. 21:117–122.
24. Parker, C. E., S. Daenke, S. Nightingale, and C. R. M. Bangham. 1992. Activated, HTLV-I-specific cytotoxic T-lymphocytes are found in healthy seropositive as well as in patients with tropical spastic paraparesis. Virol. 188:628–636.
25. Radonovich, M., and K. T. Jeang. 1989. Activation of the human T-cell leukemia virus type I long terminal repeat by 12-O-tetradecanoylphorbol-13-acetate and by tax (p40x) occurs through similar but functionally distinct target sequences. J. Virol. 63:2987–2994.
26. Reiss, P., A. deRonde, J. M. A. Lange, F. deWolf, J. Dekker, C. Debouck, and J. Goudsmit. 1989 Low antigenicity of HIV-1 rev: rev-specific antibody response of limited value as correlate of rev gene expression. AIDS Res. Human Retro. 5:621–628.
27. Semmes, O. J., and K. Jeang. 1992. Mutational analysis of human T-cell leukemia virus type I tax: regions necessary for function determined with 47 mutant proteins. J. Virol. 66:7183–7192.
28. Shioiri, S., N. Tachibana, A. Okayama, S. Ishihara, K. Tsuda, M. Essex, S. O. Stuver, and N. Mueller. 1993. Analysis of anti-tax antibody of HTLV-I carriers in an endemic area in Japan. Int. J. Cancer 53:1–4.
29. Smith M. R., and W. C. Green. 1990. Identification of HTLV-I tax trans-activator mutants exhibiting novel transcriptional phenotypes. Genes Develop. 4:1875–1885.
30. Smith, M. R, and W. C. Green. 1991. Molecular biology of the type I human T-cell leukemia virus (HTLV-I) and adult T-cell leukemia. J. Clin. Invest. 87:761–766.
31. Sonoda, S. 1990. Genetic and immunologic determinants of HTLV-I-associated diseases. In: Human retrovirology: HTLV. Blattner W. A. ed. Raven Press Ltd. NY, p.315–326.
32. Tanaka, Y., A. Yoshida, H. Tozawa, H. Shida, H. Nyunoya, and K. Shimotohno. 1991. Production of a recombinant human T-cell leukemia virus type-I trans-activator ($tax_1$)antigen and its utilization for generation of monoclonal antibodies against various epitopes on the $tax_1$ antigen. Int. J. Cancer 48:623–630.
33. Tendler, C. L., S. J. Greenberg, W. A. Blattner, A. Manns, E. Murphy, T. Fleisher, B. Hanchard, O. Morgan, J. D. Burton, D. L. Nelson, and T. A. Waldmann. (1990). Transactivation of interleukin 2 and its receptor induces immune activation in human T-cell lymphotropic virus type I-associated myelopathy: pathogenic implications and a rationale for immunotherapy. Proc. Natl. Acad. Sci. USA. 87:5218–5222.
34. Weichselbraun, I., J. Berger, M. Dobrovnik, H. Bogerd, R. Grassmann, W. C. Greene, J. Hauber, and E. Bohnlein. 1992. Dominant-negative mutants are clustered in a domain of the human T-cell leukemia virus type I rex protein: Implication for trans dominance. J. Virol. 66:4540–4545.
35. Wieland, U., J. E. Kuhn, C. Jassoy, H. Rubsamen-Waigmann, V. Wolber, and R. Braun. 1990. Antibodies to recombinant HIV-1 vif, tat, and nef proteins in human sera. Med. Microbiol. Immunol. 179:1–11.
36. Yodoi. J., and T. Uchiyama. 1992. Diseases associated with HTLV-I virus: IL-2 receptor dysregulation, and redox regulation. Immunol. Today 13:405–411.
37. Yokota, T., M. J. Cho, N. Tachibana, M. F. McLane, K. Takatsuki, T. H. Lee, N. Mueller N, and M. Essex. 1989. The prevalence of antibody to p42 of HTLV-I among ATLL patients in comparison with healthy carriers in Japan. Int. J. Cancer 43:970–974.
38. Zhao, L. J., and C. Z. Giam. 1991. Interaction of human T-cell lymphotropic virus type I (HTLV-I) transcriptional activator tax with cellular factors that bind specifically to the 21-base-pair repeats in HTLV-I enhancer. Proc. Natl. Acad. Sci. USA. 88:11445–11449.
39. Khabbaz RF, Onorato IM, Cannon RO, et al. Seroprevalence of HTLV-I and HTLV-II among intravenous drug users and persons in clinics for sexually transmitted diseases. N Eng J Med 1992;326:375–80.
40. Cullen BR. Mechanism of action of regulatory proteins encoded by complex retroviruses. Rev Microbiol 1992;56:375–394.
41. Sodroski J. The human T-cell leukemia virus (HTLV) transactivator (tax) protein. Biochem Biophys Acta 1992;1114:19–29.
42. Sawada T, Tohmatsu J, Obara T, et al. High risk of mother-to-child transmission of HTLV-I in $p40^{tax}$ antibody positive mothers. Jap J Cancer Res 1989;80:506–508.
43. Hirata M, Hayashi J, Noguchi A, et al. The effects of breast feeding and presence of antibody to $p40^{tax}$ protein of human T-lymphotropic virus type-I on mother-to-child transmission. Int J Epidemiol 1992;21:989–994.
44. Okayama A, Korber B, Chen YA, et al. Unusal patterns of antibodies to human T-leukemia virus type I in family members of adult T-cell leukemia virus type I in family members of adult T-cell leukemia patients. Blood 1991;78:3323–3329.
45. Tanaka Y, Masuda M, Yoshida A, Shida H, Nyunoya H, Shimotohno K and Tozawa H. An antigenic structure of the trans-activator protein encoded by human T-cell leukemia virus type-I (HTLV-I), as defined by a panel of monoclonal antibodies. AIDS Res. Human Retro 1992;8:227–35.

46. Rudolph DL and Lal RB. Discrimination of human T-lymphotropic virus type-I and type-II infections by synthetic peptides comprising structural epitopes from the envelope glycoproteins. Clin Chem 1993;39:288–92.

47. Brodine SK, Kaime M, Roberts C, Turnicky RP, and Lal RB. Simultaneous confirmation and differentiation of human T-lymphotropic virus type I and II infections by using recombinant proteins comprising immunodominant epitopes. Transfusion (In press).

48. Kamishira S, Toriya K, Amagasaki T, et al. Antibodies against p40$^{tax}$ gene product of human T-lymphotropic virus type I (HTLV-I) under various conditions of HTLV-I infection. Jpn J Cancer Res 1989;80:1066–1071.

49. Hollesburg P, and Hafler DA. 1993. Pathogenesis of diseases induced by human lymphotropic virus type I infection. N Engl J Med 1993; 328:1173–1182.

50. Itoyama Y, Minato S, Kira J, et al. Spontaneous proliferation of peripheral blood lymphocytes increased in patients with HTLV-I associated myelopathy. Neurology 1988;38:1302–1307.

51. Jacobson S, Shida H, McFarlin DE, Fauci AS, and Koenig S. Circulating CD8+ cytotoxic T lymphocytes specific for HTLV-I pX in patients with HTLV-I associated neurological disease. Nature 1990;348:245–248.

---

What is claimed is:

1. An antigenic peptide consisting of the amino acid sequence defined in the sequence listing by SEQ ID NO: 1.

2. An antigenic peptide consisting of the amino acid sequence defined in the sequence listing by SEQ ID NO: 2.

3. An antigenic peptide consisting of the amino acid sequence defined in the sequence listing by SEQ ID NO: 3.

4. An antigenic peptide consisting of the amino acid sequence defined in the sequence listing by SEQ ID NO: 4.

5. An antigenic peptide consisting of the amino acid sequence defined in the sequence listing by SEQ ID NO: 5.

6. An antigenic peptide consisting of the amino acid sequence defined in the sequence listing by SEQ ID NO: 6.

7. An antigenic peptide consisting of the amino acid sequence defined in the sequence listing by SEQ ID NO: 7.

8. An antigenic peptide consisting of the amino acid sequence defined in the sequence listing by SEQ ID NO: 8.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Leu Gln Ala Met Arg Lys Tyr Ser Pro Phe Arg Asn Gly Tyr Met Glu
1               5                   10                  15

Pro Thr Leu Gly
            20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Pro Ile Ser Leu Leu Phe Asn Glu Lys Glu Ala Asp Asp Asn Asp His
1               5                   10                  15

Glu Pro Gln Ile
            20
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
His Glu Pro Gln Ile Ser Pro Gly Gly Leu Glu Pro Pro Ser Glu Lys
1               5                   10                  15

His Phe Arg Glu
            20
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ser  Pro  Gly  Gly  Leu  Glu  Pro  Pro  Ser  Glu  Lys  His  Phe  Arg  Glu  Thr
1                  5                            10                           15
Glu  Val
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met  Pro  Lys  Thr  Arg  Arg  Arg  Pro  Arg  Arg  Ser  Gln  Arg  Lys  Arg  Pro
1                  5                            10                           15
Pro  Thr  Pro  Trp
                20
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Pro  Pro  Thr  Pro  Trp  Pro  Thr  Ser  Gln  Gly  Leu  Asp  Arg  Val  Phe  Phe
1                  5                            10                           15
Ser  Asp  Thr  Gln
                20
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Thr  Gly  Ala  Pro  Ser  Leu  Gly  Asp  Tyr  Val  Arg  Pro  Ala  Tyr  Ile  Val
1                  5                            10                           15
Thr  Pro  Tyr  Trp
                20
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:8:

```
Thr Pro Ser Met Asp Ala Leu Ser Ala Gln Leu Tyr Ser Ser Leu Ser
1               5                   10                  15
Leu Asp Ser Pro
            20
```

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Met Ala His Phe Pro Gly Phe Gly Gln Ser Leu Leu Phe Gly Tyr Pro
1               5                   10                  15
Val Tyr Val Phe
            20
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Pro Val Tyr Val Phe Gly Asp Cys Val Gln Gly Asp Trp Cys Pro Ile
1               5                   10                  15
Ser Gly Gly Leu
            20
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Ile Ser Gly Gly Leu Cys Ser Ala Arg Leu His Arg His Ala Leu Leu
1               5                   10                  15
Ala Thr Cys Pro
            20
```

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Leu Ala Thr Cys Pro Glu His Gln Ile Thr Trp Asp Pro Ile Asp Gly
1               5                   10                  15

Arg Val Ile Gly
            20
```

( 2 ) INFORMATION FOR SEQ ID NO:13:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:13:

```
Gly Arg Val Ile Gly Ser Ala Leu Gln Phe Leu Ile Pro Arg Leu Pro
1               5                   10                  15

Ser Phe Pro Thr
            20
```

( 2 ) INFORMATION FOR SEQ ID NO:14:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:14:

```
Pro Ser Phe Pro Thr Gln Arg Thr Ser Lys Thr Leu Lys Val Leu Thr
1               5                   10                  15

Pro Pro Ile Thr
            20
```

( 2 ) INFORMATION FOR SEQ ID NO:15:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:15:

```
Thr Pro Pro Ile Thr His Thr Thr Pro Asn Ile Pro Pro Ser Phe Leu
1               5                   10                  15

Gln Ala Met Arg
            20
```

( 2 ) INFORMATION FOR SEQ ID NO:16:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:16:

```
Glu Pro Thr Leu Gly Gln His Leu Pro Thr Leu Ser Phe Pro Asp Pro
1               5                   10                  15

Gly Leu Arg Pro
            20
```

( 2 ) INFORMATION FOR SEQ ID NO:17:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Pro  Gly  Leu  Arg  Pro  Gln  Asn  Leu  Tyr  Thr  Leu  Trp  Gly  Gly  Ser  Val
1                 5                           10                          15

Val  Cys  Met  Tyr
               20
```

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Val  Val  Cys  Met  Tyr  Leu  Tyr  Gln  Leu  Ser  Pro  Pro  Ile  Thr  Trp  Pro
1                 5                           10                          15

Leu  Leu  Pro  His
               20
```

( 2 ) INFORMATION FOR SEQ ID NO:19:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Pro  Leu  Leu  Pro  His  Val  Ile  Phe  Cys  His  Pro  Gly  Gln  Leu  Gly  Ala
1                 5                           10                          15

Phe  Leu  Thr  Asn
               20
```

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Ala  Phe  Leu  Thr  Asn  Val  Pro  Tyr  Lys  Arg  Ile  Glu  Glu  Leu  Leu  Tyr
1                 5                           10                          15

Lys  Ile  Ser  Leu
               20
```

( 2 ) INFORMATION FOR SEQ ID NO:21:

( i ) SEQUENCE CHARACTERISTICS:
        ( A ) LENGTH: 20 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:21:

```
Tyr Lys Ile Ser Leu Thr Thr Gly Ala Leu Ile Ile Leu Pro Glu Asp
 1               5                  10                  15
Cys Leu Pro Thr
            20
```

(2) INFORMATION FOR SEQ ID NO:22:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Asp Cys Leu Pro Thr Thr Leu Phe Gln Ala Arg Ala Ala Pro Val Thr
 1               5                  10                  15
Leu Thr Ala Trp
            20
```

(2) INFORMATION FOR SEQ ID NO:23:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Thr Leu Thr Ala Trp Gln Asn Gly Leu Leu Pro Phe His Ser Thr Leu
 1               5                  10                  15
Thr Thr Pro Gly
            20
```

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Leu Thr Thr Pro Gly Leu Ile Trp Thr Phe Thr Asp Gly Thr Pro Met
 1               5                  10                  15
Ile Ser Gly Pro
            20
```

(2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Met  Ile  Ser  Gly  Pro  Cys  Pro  Lys  Asp  Gly  Gln  Pro  Ser  Leu  Val  Leu
1                  5                        10                       15

Gln  Ser  Ser  Ser
               20
```

( 2 ) INFORMATION FOR SEQ ID NO:26:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Leu  Gln  Ser  Ser  Ser  Phe  Ile  Phe  His  Lys  Phe  Gln  Thr  Lys  Ala  Tyr
1                  5                        10                       15

His  Pro  Ser  Phe
               20
```

( 2 ) INFORMATION FOR SEQ ID NO:27:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Tyr  His  Pro  Ser  Phe  Leu  Leu  Ser  His  Gly  Leu  Ile  Gln  Tyr  Ser  Ser
1                  5                        10                       15

Phe  His  Ser  Leu
               20
```

( 2 ) INFORMATION FOR SEQ ID NO:28:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Ser  Phe  His  Ser  Leu  His  Leu  Leu  Phe  Glu  Glu  Tyr  Thr  Asn  Ile  Pro
1                  5                        10                       15

Ile  Ser  Leu  Leu
               20
```

( 2 ) INFORMATION FOR SEQ ID NO:29:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Phe  Ser  Asp  Thr  Gln  Ser  Thr  Cys  Leu  Glu  Thr  Val  Tyr  Lys  Ala  Thr
1                  5                        10                       15

Gly  Ala  Pro  Ser
               20
```

( 2 ) INFORMATION FOR SEQ ID NO:30:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Val  Thr  Pro  Tyr  Trp  Pro  Pro  Val  Gln  Ser  Ile  Arg  Ser  Pro  Gly  Thr
1                   5                        10                       15
Pro  Ser  Met  Asp
               20
```

( 2 ) INFORMATION FOR SEQ ID NO:31:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Ser  Leu  Asp  Ser  Pro  Pro  Ser  Pro  Pro  Arg  Glu  Pro  Leu  Arg  Pro  Ser
1                   5                        10                       15
Arg  Ser  Leu  Pro
               20
```

( 2 ) INFORMATION FOR SEQ ID NO:32:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
Ser  Arg  Ser  Leu  Pro  Arg  Gln  Ser  Leu  Ile  Gln  Pro  Pro  Thr  Phe  His
1                   5                        10                       15
Pro  Pro  Ser  Ser
               20
```

( 2 ) INFORMATION FOR SEQ ID NO:33:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
His  Pro  Pro  Ser  Ser  Arg  Pro  Cys  Ala  Asn  Thr  Pro  Pro  Ser  Glu  Met
1                   5                        10                       15
Asp  Thr  Trp  Asn
               20
```

( 2 ) INFORMATION FOR SEQ ID NO:34:

( i ) SEQUENCE CHARACTERISTICS:
        ( A ) LENGTH: 20 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Met Asp Thr Trp Asn Pro Pro Leu Gly Ser Thr Ser Gln Pro Cys Leu
1               5                   10                  15

Phe Gln Thr Pro
            20

(2) INFORMATION FOR SEQ ID NO:35:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:35:

Leu Phe Gln Thr Pro Asp Ser Gly Pro Lys Thr Cys Thr Pro Ser Gly
1               5                   10                  15

Glu Ala Pro Leu
            20

(2) INFORMATION FOR SEQ ID NO:36:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:36:

Gly Glu Ala Pro Leu Ser Ala Cys Thr Ser Thr Ser Phe Pro Pro Pro
1               5                   10                  15

Ser Pro Gly Pro
            20

(2) INFORMATION FOR SEQ ID NO:37:

(i) SEQUENCE CHARACTERISTICS:
    (A) LENGTH: 13 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:37:

Ser Phe Pro Pro Pro Ser Pro Gly Pro Ser Cys Pro Thr
1               5                   10

(2) INFORMATION FOR SEQ ID NO:38:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:38:

Lys Tyr Ser Pro Ser Arg Asn Gly Tyr Met (2) INFORMATION FOR SEQ ID NO:39:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

His Glu Pro Gln Ile Ser Pro Gly Gly Leu Glu
    1               5                   10

(2) INFORMATION FOR SEQ ID NO:40:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Ser Pro Gly Gly Leu Glu Pro Pro Ser Glu Lys His Phe Arg Glu
    1               5                   10                  15